United States Patent
Dinan et al.

(10) Patent No.: US 6,855,729 B2
(45) Date of Patent: Feb. 15, 2005

(54) TREATMENT OF FIBROMYALGIA AND RELATED FATIGUE SYNDROMES USING ANTAGONISTS OR PARTIAL AGONISTS OF 5HT1A RECEPTORS

(76) Inventors: Timothy G. Dinan, Merton House, Frenches Walk, Cobh, Co. Cork (IR); Paul W. N. Keeling, 12 Morehampton Road, Dublin (IR)

( * ) Notice: Subject to any disclaimer, the term of this patent is extended or adjusted under 35 U.S.C. 154(b) by 7 days.

(21) Appl. No.: 10/079,681

(22) Filed: Feb. 20, 2002

(65) Prior Publication Data
US 2002/0165263 A1 Nov. 7, 2002

Related U.S. Application Data

(60) Provisional application No. 60/269,937, filed on Feb. 20, 2001.

(51) Int. Cl.[7] .................. A01N 43/38; A61K 31/405
(52) U.S. Cl. .................................. 514/415; 514/418
(58) Field of Search ............................. 514/415, 418

(56) References Cited

U.S. PATENT DOCUMENTS 6,277,852 B1 * 8/2001 Howard ................. 514/252.13
6,525,196 B1 * 2/2003 Bright et al. .............. 544/295

FOREIGN PATENT DOCUMENTS

WO  WO 99/52907 A1 * 10/1999

* cited by examiner

*Primary Examiner*—Zohreh Fay
*Assistant Examiner*—Brian-Yong S. Kwon
(74) *Attorney, Agent, or Firm*—McDonnell Boehnen Hulbert & Berghoff

(57) ABSTRACT

The present invention provides a method for treating fibromyalgia and/or chronic fatigue syndrome by administering an antagonist or partial agonist of 5HT1$a$ receptors.

4 Claims, No Drawings

TREATMENT OF FIBROMYALGIA AND RELATED FATIGUE SYNDROMES USING ANTAGONISTS OR PARTIAL AGONISTS OF 5HT1A RECEPTORS

FIELD OF THE INVENTION

The present invention provides a method for treating fibromyalgia and related chronic fatigue syndromes by administering an antagonist or partial agonist of 5HT1a receptors.

Fibromyalgia is a common clinical condition presenting with musculoskeletal pain and tenderness often accompanied by fatigue (Goldberg D L 1995 Curr Opin Rheumatol 7, 127–135). It is seen both in Primary Care and in Rheumatology Clinics. No specific treatment for the condition is available and it is frequently regarded as a functional disorder which can run a chronic course.

Fibromyalgia and chronic fatigue syndromes share many clinical characteristics. A majority of the patients are women and usually in their thirties or forties on initial presentation. Over eighty percent in both diagnostic categories complain of fatigue, myalgia, arthralgia, recurrent headache and sleep difficulties (Moldofsky, 1993 Ciba Symposium 173 p 262–279).

Conventional diagnostic evaluation does not reveal a structural or biochemical abnormality in either fibromyalgia or related chronic fatigue syndrme. Attempts at elucidating the pathophysiology have produced inconsistent findings and a wide array of theories are currently put forward.

Studies indicate that a central 5HT1a receptor hypersensitivity may be involved in the pathophysiology of chronic fatigue syndrome and/or fibromyalgia (Bakheit A M, Behan P O, Dinan T G 1992 British Medical Journal 304, 245–252). The release of prolactin from the anterior pituitary is under dopamine inhibition and under 5HT stimulation, probably at the level of the hypothalamus (Lamberts S W J, Macleod R M. Regulation of prolactin secretion at the level of the lactrotroph. Physiol Rev. 1990;70:279–318.). Buspirone is an azaspirodecanedione, which acts as a partial agonist at the 5HT1a receptor (Meltzer H Y, Maes M. Effects of buspirone on plasma prolactin and cortisol levels in major depressed and normal subjects. Biol Psychiat. 1994;35:316–323) and stimulates prolactin release. We have established that prolactin release following buspirone challenge is enhanced in patients fulfilling criteria for chronic fatigue syndrome and fibromyalgia indicating 5HT1a receptor supersensitivity in these conditions.

We have demonstrated this in a clinical study that extends our previous findings reported in U.S. Pat. No. 5,403,848 which relates to non-ulcer dyspepsia.

A total of 12 subjects (9 female/3 male) and 12 healthy comparison subjects (9 female/3 male) gave fully informed consent to take part in the study. The mean±SD age of the patients was 33.6±8.2 years (Range 22–41) and of the comparison group 28.2±8.6 years (Range 20–45). All patients fulfilled criteria for both fibromyalgia (ACR criteria) and chronic fatigue syndrome (CDC criteria). At 0830 h subjects had a cannula inserted in a forearm vein. Buspirone (30 mg) or matching placebo was administered orally at 0900 h (Time 0). Blood was taken at 0, 30, 60, 90, 120 and 180 min. Prolactin levels rose in all subjects challenged with buspirone. The mean±SD AUC in patients was 49±28 and in healthy subjects 27±35. This difference is significant at the 0.05 level. Prolactin concentration between 60 and 90 min following buspirone administration provided the best discrimination between the two groups.

According to the present invention, what is required to treat fibromyagia and/or chronic fatigue syndrome is the administration of effective amounts of a substance that reduces the sensitivity of 5HT1a receptors and we have discovered that pindolol, which has affinity for 5HT1a receptors has beneficial effects in subjects suffering from fibromyalgia and/or chronic fatigue syndrome.

SUMMARY OF THE INVENTION

The present invention provides a means for prevention and treatment of fibromyalgia and/or chronic fatigue syndrome by administration of a substance that reduces the sensitivity of 5HT1a receptors. A preferred means is the administration of RS pindolol or a salt thereof An especially preferred means is the administration of S (−) pindolol or a salt thereof.

DETAILED DESCRIPTION OF THE INVENTION

As noted earlier, this invention can use any substance that is an antagonist or a partial agonist of 5HT1a receptors such that the sensitivity of 5HT1a receptors described above is reduced.

Pindolol is a beta adrenergic antagonist, used in the treatment of hypertension and angina. It also has affinity for 5HT1a receptors of a similar magnitude as its affinity for beta adrenergic receptors. Until now, no therapeutic applications of this phenomenon have been discovered. Pindolol is used therapeutically in hypertension and angina as the racemic substance, RS pindolol. Most or all of the pharmacological effects of pindolol are possessed by the isomer S (−) pindolol. The present invention utilizes pindolol to reduce the sensitivity of 5HT1a receptors and as a result to provide the means for prevention and treatment of certain fatigue syndromes including fibromyalgia. A preferred embodiment of the invention is the isomer S (−) pindolol or salts thereof.

The invention is likely to be effective in various presentations of fibromyalgia and/or chronic fatigue syndrome in which there is altered sensitivity of 5HT1a receptors.

Various pharmaceutical presentations are possible, including (but not limited to) tablets, capsules, oral solutions and suspensions and parenteral solutions. Included are also pharmaceutical formulations for oral use in which the active substance is released in a controlled and slower fashion such that the treatment may be administered less frequently.

The usual doses of RS pindolol and S (−) pindolol will be in the range of 2.5 mg to 50 mg daily in single or divided doses, depending upon the therapeutic response and the pharmaceutical form. The usual doses of S (−) pindolol will be lesser than those of RS pindolol since the former will be more potent because it is responsible for most or all of the pharmacological effects.

The invention is intended for the treatment of mammals, including humans.

The ability of the invention to treat gastrointestinal disease has been demonstrated in a clinical study.

REFERENCES TO PREVIOUS PATENTS

T. G. Dinan and P. W. N. Keeling U.S. Pat. No. 5,324,783
T. G. Dinan and P. W. N. Keeling U.S. Pat. No. 5,403,848

EXAMPLE

Five patients with fibromyalgia (ACR criteria) who also met criteria for chronic fatigue syndrome (CDC criteria)

gave informed consent to take part in this open label treatment study. All were treated with pindolol 2.5 mg three times daily. Four of 5 patients showed a significant improvement in symptoms within 10 days of commencing treatment. There was a reduction in all symptoms and an increase in energy levels and general wellbeing.

What is claimed is:

1. A method for treating fibromyalgia comprising administering of an effective amount of an antagonist or partial agonist of 5HT1a receptors which is an effective amount of the racemic substance RS pindolol or a salt thereof.

2. A method for treating fibromyalgia comprising administering an effective amount of one of the enantiomers, S(−) pindolol or a salt thereof.

3. A method for treating fibromyalgia comprising administering effective amounts of RS-pindolol or S(−) pindolol or their salts are administered in a pharmaceutical dosage form that permits rapid release of the active substances.

4. A method for treating fibromyalgia comprising administrating of an effective amount of an antagonist or partial agonist of 5HT1a receptors in which effective amounts of RS pindolol or S(−) pindolol or their salts are administered in a pharmaceutical dosage form that releases the active substances in a controlled release form.

* * * * *